United States Patent [19]
Dean et al.

[11] Patent Number: 5,997,845
[45] Date of Patent: *Dec. 7, 1999

[54] TECHNETIUM-99M LABELED PEPTIDES FOR IMAGING INFLAMMATION

[75] Inventors: Richard T. Dean; John Lister-James, both of Bedford, N.H.; Edgar R. Civitello, Flagstaff, Ariz.

[73] Assignee: Diatide, Inc., Londonderry, N.H.

[*] Notice: This patent is subject to a terminal disclaimer.

[21] Appl. No.: 08/902,367

[22] Filed: Jul. 29, 1997

Related U.S. Application Data

[60] Continuation of application No. 08/462,668, Jun. 5, 1995, abandoned, which is a division of application No. 08/439,905, May 12, 1995, Pat. No. 5,645,815, which is a continuation of application No. 08/044,825, Apr. 8, 1993, abandoned, which is a continuation-in-part of application No. 07/653,012, Feb. 8, 1991, abandoned, said application No. 08/469,858, Jun. 6, 1995, is a division of application No. 07/893,981, Jun. 5, 1992, Pat. No. 5,508,020, said application No. 08/273,274, Jul. 11, 1994, Pat. No. 5,849,260, is a continuation of application No. 07/886,752, May 21, 1992, abandoned.

[51] Int. Cl.⁶ ............................ A61K 51/00; A61M 36/14
[52] U.S. Cl. .................. 424/1.69; 424/1.11; 424/1.65; 530/300; 530/324; 530/325; 530/326; 530/327; 530/328; 530/329; 530/330; 534/10; 534/14
[58] Field of Search ..................... 424/1.11, 1.37, 424/1.49, 1.53, 1.65, 1.69, 9.1, 9.3, 9.4, 9.5; 530/300, 324–330, 333–334, 338; 534/7, 10–16; 206/223, 569, 570

[56] References Cited

U.S. PATENT DOCUMENTS

| | | |
|---|---|---|
| 4,434,151 | 2/1984 | Byrne et al. . |
| 4,444,690 | 4/1984 | Fritzberg et al. . |
| 4,472,509 | 9/1984 | Gansow et al. . |
| 4,571,430 | 2/1986 | Byrne et al. . |
| 4,575,556 | 3/1986 | Byrne et al. . |
| 4,578,079 | 3/1986 | Rouslhati et al. . |
| 4,729,525 | 3/1988 | Rouslhati et al. . |
| 4,857,508 | 8/1989 | Adams et al. . |
| 4,861,869 | 8/1989 | Nicolotti et al. . |
| 4,986,979 | 1/1991 | Morgan et al. . |
| 5,086,069 | 2/1992 | Klein et al. ............... 514/399 |
| 5,225,181 | 7/1993 | Srivastava et al. ........... 424/1.11 |
| 5,256,559 | 10/1993 | Maraganore et al. .......... 435/240.2 |
| 5,372,933 | 12/1994 | Zamarron et al. ............ 530/326 |
| 5,395,609 | 3/1995 | Stuttle ...................... 424/1.69 |
| 5,492,890 | 2/1996 | Ginsberg et al. ............. 514/12 |
| 5,498,499 | 3/1996 | Flow et al. ................. 435/7.21 |
| 5,612,311 | 3/1997 | Pierschbacher et al. ........ 514/11 |
| 5,645,815 | 7/1997 | Dean et al. ................. 424/1.69 |
| 5,662,885 | 9/1997 | Pollak et al. ............... 424/1.69 |
| 5,686,571 | 11/1997 | Scarborough et al. .......... 530/330 |
| 5,830,856 | 11/1998 | Dean et al. ................. 514/12 |

FOREIGN PATENT DOCUMENTS

| | | |
|---|---|---|
| 135160 | 3/1985 | European Pat. Off. . |
| 188256 | 7/1986 | European Pat. Off. . |
| 284071 | 9/1988 | European Pat. Off. . |
| 0 301 458 A2 | 1/1989 | European Pat. Off. . |
| 398143 | 11/1990 | European Pat. Off. . |
| 0 410 537 A1 | 1/1991 | European Pat. Off. . |
| 0 410 539 A1 | 1/1991 | European Pat. Off. . |
| 0 410 540 A1 | 1/1991 | European Pat. Off. . |
| 0 410 541 A1 | 1/1991 | European Pat. Off. . |
| 0 422 937 A1 | 4/1991 | European Pat. Off. . |
| 0 422 938 A1 | 4/1991 | European Pat. Off. . |
| 0 425 212 A2 | 5/1991 | European Pat. Off. . |
| 0 478 328 A1 | 4/1992 | European Pat. Off. . |
| WO 89/05150 | 6/1989 | WIPO . |
| WO 90/10463 | 9/1990 | WIPO . |
| WO 90/15818 | 12/1990 | WIPO . |
| WO 91/01331 | 2/1991 | WIPO . |
| WO 91/15515 | 10/1991 | WIPO . |
| WO 91/17173 | 11/1991 | WIPO . |
| 9323085 | 11/1993 | WIPO . |
| 9423758 | 10/1994 | WIPO . |
| WO 9422494 | 10/1994 | WIPO ........................... A61K 49/02 |
| 9533496 | 12/1995 | WIPO . |

OTHER PUBLICATIONS

Rhodes, 1974, "Considerations in the Radiolabeling of Albumin", *Sem. Nucl. Med.* 4: 281–293.

Davidson et al., 1981, "A New Class of Oxotechnetium(5+) Chelate Complexes containing a $TcON_2S_2$ Core", *Inorg. Chem.* 20: 1629–1632.

Fritzberg et al., 1982, "Synthesis and Biological Evaluation of Tc–99m N,N'–Bis(mercaptoacetyl)–2,3–diaminopropanoate: A Potential Replacement for [$^{131}$I]0–iodohippurate", *J. Nucl. Med.* 23: 592–598.

Fritzberg et al., 1982, "Clinical comparison of Tc–99m N,N'–bis(mercaptoacetamido)ethylenediamine and ($^{131}$I)ortho–iodohippurate for evaluation of renal tubular function: Concise Communication", *J. Nucl. Med.* 23: P17.

Khaw et al., 1982, "Technetium–99m Labeling of Antibodies to Cardiac Myosin Fab and to Human Fibrinogen", *J. Nucl. Med.* 23: 1011–1019.

Byrne and Tolman, 1983, "Technetium–99m Bifunctional Chelating Agent—Thiolactone for Coupling to Biomolecules, $N_2S_2$ Ligand for Chelation to Technetium", *J. Nucl. Med.* 24: P126.

Bryson et al., 1988, "Neutral Technetium(V) Complexes with Amide–Thiol–Thioether Chelating Ligands", *Inorg. Chem.* 27: 2154–2161.

(List continued on next page.)

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled scintigraphic imaging agents, and methods and reagents for producing such agents. Specifically, the invention relates to specific binding compounds, including peptides, that bind to a platelet receptor that is the platelet GPIIb/IIIa receptor, methods and kits for making such compounds, and methods for using such compounds labeled with technetium-99m via a covalently-linked radiolabel-binding moiety to image thrombi in a mammalian body.

5 Claims, No Drawings

OTHER PUBLICATIONS

Bryson et al., 1990, "Protecting Groups in the Preparation of Thiolate Complexes of Technetium", Inorg. Chem. 29: 2948–2951.

Knight et al., 1990, "Thrombus Imaging with Tc–99m Synthetic peptides Reactive with Activated Platelets", J. Nucl. Med. 31: 757 #209.

Deuel et al., 1977, Proc. Natl. Acad. Sci. USA 74: 2256–2258 disclose the amino acid sequence of human platelet factor 4.

Niedel and Cuatrecasas, 1980, Formyl Peptide Chemotactic Receptors of Leukocytes and Macrophages, in Curr. Top. Cell. Reg. 17: 137–170 disclose that formyl–methionyl–leucyl–phenylalanyl peptides cause superoxide release from neutrophils.

Deuel et al., 1981, Proc. Natl. Acad. Sci. USA 78: 4584–4587 disclose that platelet factor 4 is chemotactic for neutrophils and monocytes in vitro.

Zoghbi et al., 1981, J. Nucl. Med. 22: 32 (Abst) disclose formyl peptide chemotactic factors (fMLF) derived from bacteria coupled to $^{111}$In–labeled transferrin.

Jiang et al., 1982, Nuklearmedizin 21: 110–113 disclose a chemotactic formylated peptide (fMLF) radiolabeled with $^{125}$I.

Osterman et al., 1982, Biochem. Biophys. Res. Comm. 107: 130–135 disclose that the carboxyl–terminal tridecapeptide of platelet factor 4 has chemotactic properties.

Holt & Niewiarowski, 1985, Sem. Hematol. 22: 151–163 provide a review of the biochemistry of platelet α–granule proteins, including platelet factor 4.

Goldman et al., 1985, Immunol. 54: 163–171 reveal that fMLF receptor–mediated uptake is inhibited in human neutrophils by platelet factor 4 and a carboxyl–terminal dodecapeptide thereof.

Loscalzo et al., 1985, Arch. Biochem. Biophys. 240: 446–455 describe the biochemical interaction between platelet factor 4 and glycosaminoglycans such as heparin.

Bebawy et al., 1986, J. Leukocyte Biol. 39: 423–434 describe the platelet factor 4–mediated chemotactic response of neutrophils in vitro.

Wilkinson, 1988, Meth. Enzymol. 162: 127–132 discloses a method for characterizing chemotactic peptides capable of causing leukocytes to move up a peptide concentration gradient.

Vorne et al., 1989, J. Nucl. Med. 30: 1332–1336 disclose the use of Tc–99m labeled leukocytes for imaging sites of infection.

LaMuraglia et al., 1989, J. Vasc. Surg. 10: 20–28 disclose the use of $^{111}$In–labeled non–specific human immunoglobulin to detect sites of inflammation in vivo.

Maione et al., 1989, Science 247: 77–79 disclose that angiogenesis is inhibited by recombinant human platelet factor 4 and peptide fragments thereof.

Lind et al., 1990, J. Nucl. Med. 31: 417–473 disclose the use of Tc–99m labeled antigranulocyte monoclonal antibodies to detect inflammation.

Fischman et al., 1991, J. Nucl. Med. 32: 482–491 relates to chemotactic formyl peptide (fMLF)—$^{111}$In–labeled DTPA conjugates.

Hartman et al., 1992, "Non–peptide fibrinogen receptor antagonists: 1. Discovery and design of exosite inhibitors", J. Med. Chem. 35: 4640–4642.

Ojima et al., 1992, "Design and Synthesis of New RGD Peptides as Inhibitors of Human Platelet Aggregation", 204th Meeting, Amer. Chem. Soc. Abst. 44.

Knight, 1990, "Radiopharmaceuticals for Thrombus Detection", Sem. Nucl. Med. 20: 52–67.

Plow et al., 1987, in *Perspectives in Inflammation, Neoplasia and Vascular Cell Biology*, pp. 267–275.

Pearson et al (1996), J. Med. Chem, vol.39, No. 7, pp. 1372–1382, Thrombus Imaging Using Technetium–99m Labeled High Potency GPIIb/IIIa Receptor Antagonists. Chemistry and Initial Biological Studies.

5,997,845

TECHNETIUM-99M LABELED PEPTIDES FOR IMAGING INFLAMMATION

This application is a continuation of U.S. patent application Ser. No. 08/462,668, filed Jun. 5, 1995 and now abandoned, which is a divisional of U.S. patent application Ser. No. 08/439,905, filed May 12, 1995 and now U.S. Pat. No. 5,645,815, which is a continuation of U.S. patent application Ser. No. 08/044,825, filed Apr. 8, 1993 and now abandoned, which is a continuation-in-part of U.S. patent application Ser. No. 07/653,012, filed Feb. 8, 1991 and now abandoned; and this application is also a continuation-in-part of allowed U.S. Ser. No. 08/469,858, filed Jun. 6, 1995, which is a division of U.S. Ser. No. 07/893,981, filed Jun. 5, 1992 and now U.S. Pat. No. 5,508,020; this application is also a continuation-in-part of U.S. Ser. No. 08/273,274, filed Jul. 11, 1994 and now U.S. Pat. No. 5,849,260, which is a continuation of U.S. Ser. No. 07/886,752, filed May 21, 1992 and now abandoned.

BACKGROUND OF THE INVENTION

1. Field of the Invention

This invention relates to scintigraphic imaging agents and reagents, and methods for producing such agents and reagents. Specifically, the invention relates to reagents that can be radiolabeled with technetium-99m (Tc-99m), methods and kits for making and radiolabeling such reagents, and methods for using such radiolabeled reagents to image sites of thrombus formation in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths (J. Seabold, Society of Nuclear Medicine Annual Meeting 1990). It has also been estimated that over 90% of all pulmonary emboli arise from DVT in the lower extremities. Anticoagulant therapy can effectively treat these conditions if applied early enough. However, such treatment is associated with risks (e.g. internal bleeding) that prevent unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of localizing thrombi in vivo, most preferably using non-invasive methods, is highly desirable. Methods currently utilized for the identification of sites of deep-vein thrombosis are contrast venography and compression B-mode ultrasound; the choice of which technique is used depends on the expected location of the thrombus. However, the former technique is invasive and both techniques are uncomfortable for the patient. In addition, these methods are in many cases either unsuitable or yield inaccurate results.

Current methods used to diagnose PE include chest X-ray, electrocardiogram (EKG), areterial oxygen tension, perfusion and ventilation lung scans, and pulmonary angiography. Apart from the latter (invasive) procedure, none of these methods is capable of providing an unequivocal diagnosis.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

A variety of radionuclides are known to be useful for radioimaging, including $^{67}$Ga, $^{68}$Ga, $^{99m}$Tc (Tc-99m), $^{111}$In, $^{123}$I, $^{125}$I, $^{169}$Yb and $^{186}$Re. Of these radionuclides, Tc-99m and $^{111}$In are preferred single photon-emitting radionuclides and $^{68}$Ga is preferred as a positron-emitting radionuclide. Tc-99m is a preferred radionuclide because it emits gamma radiation at 140 keV, it has a physical half-life of 6 hours, and it is readily available on-site using a molybdenum-99/technetium-99m generator.

A gamma-emitting radiotracer that binds specifically to a component of a thrombus in preference to other tissues when administered in vivo can provide an external scintigraphic image which defines the location of the thrombus-bound radiotracer and hence the thrombus. Thrombi are constructs of blood cells, largely activated platelets, enmeshed in cross-linked fibrin. Activated platelets are particularly good targets for radioimaging thrombi because they are not normally found in circulating blood (which contains unactivated platelets).

Activated platelets express the GPIIb/IIIa receptor on their cell surfaces. The normal ligand for this receptor is fibrinogen (Plow et al., 1987, *Perspectives in Inflammation, Neoglasia and Vascular Cell Biology*, pp. 267–275). However, small, synthetic analogues, which may be but are not necessarily peptides, have been developed that bind to this receptor (examples include Klein et al., 1992, U.S. Pat. No. 5,086,069 and Egbertson et al., 1992, European Patent Application No. EPA 0478328A1). Although many of these synthetic molecules bind with only low affinity, others have been made that have very high affinity (see Egbertson et al., ibid.). This invention provides small, synthetic, radiolabeled (preferably Tc-99m, $^{111}$In or $^{68}$Ga labeled) compounds that bind to the GPIIb/IIIa receptor with high affinity, as scintigraphic agents for non-invasive imaging of thrombi in vivo.

Attempts to provide radiotracers for imaging thrombi are known in the prior art. These include autologous platelets, labeled with either $^{111}$In or $^{99m}$Tc (Tc-99m), and $^{123}$I- and $^{125}$I-labeled fibrinogen (the latter detected with a gamma scintillation probe as opposed to a gamma camera). Additional radiolabeled compounds used to label thrombi include plasmin, plasminogen activators, heparin, fibronectin, fibrin Fragment $E_1$ and anti-fibrin and anti-platelet monoclonal antibodies [see Knight, 1990, Sem. Nucl. Med. 20: 52–67 for review].

Compounds having the ability to bind to the platelet GPIIb/IIIa receptor are known in the prior art.

Ruoslahti & Pierschbacher, U.S. Pat. No. 4,578,079 describe peptides of sequence X-Arg-Gly-Asp-R-Y, wherein X and Y are either H or an amino acid, and R is Thr or Cys, the peptides being capable of binding to platelets.

Ruoslahti & Pierschbacher, U.S. Pat. No. 4,792,525 describe peptides of sequence Arg-Gly-Asp-X, wherein X is Ser, Thr or Cys, the peptides being capable of binding to platelets.

Klein et al., 1992, U.S. Pat. No. 5,086,069 disclose guanine derivatives that bind to the GPIIb/IIIa receptor.

Pierschbacher et al., 1989, PCT/US88/04403 disclose conformationally-restricted RGD-containing peptides for inhibiting cell attachment to a substratum.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Pierschbacher et al., 1991, PCT/US91/02356 disclose cyclic peptides that are fibrinogen receptor antagonists.

Egbertson et al., 1992, European Patent Application 0478328A1 disclose tyrosine derivatives that bind with high affinity to the GPIIb/IIIa receptor.

Ojima et al., 1992, 204th Meeting, Amer. Chem. Soc. Abst. 44 disclose synthetic multimeric RDGF peptides useful in inhibiting platelet aggregation.

Hartman et al., 1992, J. Med. Chem. 35: 4640–4642 describe tyrosine derivatives that have a high affinity for the GPIIb/IIIa receptor.

Radiolabeled peptides for radioimaging thrombi have been reported in the prior art.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Rodwell et al., 1991, PCT/US91/03116 disclose conjugates of "molecular recognition units" with "effector domains".

The use of chelating agents for radiolabeling polypeptides, and methods for labeling peptides and polypeptides with Tc-99m are known in the prior art and are disclosed in 07/653,012, now abandoned, a divisional of which issued as U.S. Pat. No. 5,654,272; 07/807,062, now U.S. Pat. No. 5,443,815; 07/871,282, a divisional of which issued as U.S. Pat. No. 5,780,007; 07/886,752, now abandoned, a divisional of which issued as U.S. Pat. No. 5,736,122; and 07/893,981, now U.S. Pat. No. 5,508,020.

There remains a need for small (to enhance blood and background tissue clearance), synthetic (to make routine manufacture practicable and to ease regulatory acceptance), high-affinity, specific-binding molecules radiolabeled with a convenient radiolabel, preferably Tc-99m, for use in imaging thrombi in vivo. Small synthetic compounds that bind specifically to the GPIIb/IIIa receptor on activated platelets, that are radiolabeled with a convenient radioisotope, preferably Tc-99m, $^{111}$In or $^{68}$Ga, fulfill this need in the art, and are provided by this invention.

SUMMARY OF THE INVENTION

The present invention provides scintigraphic thrombus imaging agents that are radioactively-labeled reagents. Specifically, the invention provides reagents for preparing thrombus imaging agents that are radiolabeled with technetium-99m (Tc-99m), $^{111}$In or $^{68}$Ga, preferably with Tc-99m. The reagents of the invention are each comprised of a specific binding compound, including but not limited to peptides, that binds specifically and with high affinity to the platelet glycoprotein IIb/IIIa (GPIIb/IIIa) receptor, that is covalently linked to a radiolabel-binding moiety.

For optimal imaging, the reagent must be capable of binding to the platelet GPIIb/IIIa receptor with sufficient affinity that it inhibits the adenosine diphosphate (ADP)-induced aggregation of human platelets in a standard platelet aggregation assay (see Example 3 below) when present at a concentration of no more than 0.3 $\mu$M. Also, it is of distinct commercial advantage to use small compounds, preferably having a molecular weight of less than about 10,000 daltons. Such small compounds can be readily manufactured. Moreover, they are likely not to be immunogenic and to clear rapidly from the vasculature, thus allowing for better and more rapid imaging of thrombi. In contrast, larger molecules such as antibodies of fragments thereof, or other biologically-derived peptides larger than 10,000 daltons, are costly to manufacture, and are likely to be immunogenic and clear more slowly from the bloodstream, thereby interfering with rapid diagnoses of thrombi in vivo.

The invention also provides reagents wherein the specific binding compounds are linear or cyclic peptides having an amino acid sequence of 4 to 100 amino acids.

One aspect of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a Tc-99m binding moiety of formula:

$$C(pgp)^s\text{-}(aa)\text{-}C(pgp)^s \qquad\qquad \text{I.}$$

wherein $C(pgp)^s$ is a protected cysteine and (aa) is an amino acid. In a preferred embodiment, the amino acid is glycine.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, and that covalently linked to a Tc-99m binding moiety comprising a single thiol moiety having a formula:

$$A\text{—}CZ(B)\text{—}[C(R^1R^2)]_n\text{—}X \qquad\qquad \text{II.}$$

wherein A is H, HOOC, $H_2NOC$, (peptide)—NHOC, (peptide)—OOC or $R^4$; B is H, SH or —$NHR^3$, —$N(R^3)$-(peptide) or $R^4$; X is SH or —$NHR^3$, —$N(R^3)$-(peptide) or $R^4$; $R^1$, $R^2$, $R^3$ and $R^4$ are independently H or straight or branched chain or cyclic lower alkyl; n is 0, 1 or 2; and: (1) where B is —$NHR^3$ or —$N(R^3)$-(peptide), X is SH and n is 1 or 2; (2) where X is —$NHR^3$ or —$N(R^3)$-(peptide), B is SH and n is 1 or 2; (3) where B is H or $R^4$, A is HOOC, $H_2NOC$, (peptide)—NHOC, (peptide)—OOC, X is SH and n is 0 or 1; (4) where A is H or $R^4$, then where B is SH, X is —$NHR^3$ or —$N(R^3)$-(peptide) and where X is SH, B is —$NHR^3$ or —$N(R^3)$-(peptide); (5) where X is H or $R^4$, A is HOOC, $H_2NOC$, (peptide)—NHOC, (peptide)—OOC and B is SH; (6) where Z is methyl, X is methyl, A is HOOC, $H_2NOC$, (peptide)—NHOC, (peptide)—OOC and B is SH and n is 0; and wherein the thiol moiety is in the reduced form.

In another embodiment, the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel binding moiety of formula:

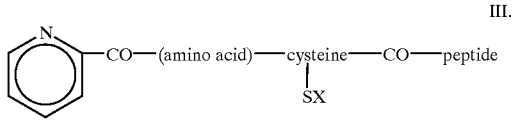

III.

[for purposes of this invention, radiolabel-binding moieties having this structure will be referred to as picolinic acid (Pic)-based moieties];

or

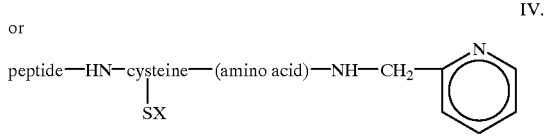

IV.

[for purposes of this invention, radiolabel-binding moieties having this structure will be referred to as picolylamine (Pica)-based moieties]; wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the peptide is covalently linked to the radiolabel-binding moiety via an amino acid, most preferably glycine.

Yet another embodiment of the invention provides a reagent for preparing a thrombus imaging agent that is capable of being radiolabeled for imaging thrombi within a mammalian body, comprising a specific binding compound that specifically binds to the platelet GPIIb/IIIa receptor, and that is covalently linked to a radiolabel-binding moiety that is a bisamino bisthiol radiolabel binding moiety. The bisamino bisthiol moiety in this embodiment of the invention has a formula selected from the group consisting of:

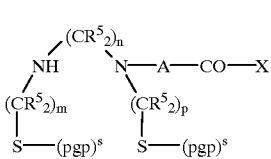

V.

wherein each $R^5$ can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is peptide; and

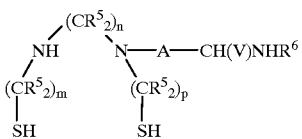

VI.

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-peptide; $R^6$ is H or peptide; provided that when V is H, $R^6$ is peptide and when $R^6$ is H, V is peptide. [For purposes of this invention, radiolabel-binding moieties having these structures will be referred to as "BAT" moieties]. In a preferred embodiment, the peptide is covalently linked to the radiolabel-binding moiety via an amino acid, most preferably glycine.

In preferred embodiments of the aforementioned aspects of this invention, the specific binding compound is a peptide is comprised of between 4 and 100 amino acids. The most preferred embodiment of the radiolabel is technetium-99m.

The reagents of the invention may be formed wherein the specific binding compounds or the radiolabel-binding moieties are covalently linked to a polyvalent linking moiety. Polyvalent linking moieties of the invention are comprised of at least 2 identical linker functional groups capable of covalently bonding to specific binding compounds or radiolabel-binding moieties. Preferred linker functional groups are primary or secondary amines, hydroxyl groups, carboxylic acid groups or thiol-reactive groups. In preferred embodiments, the polyvalent linking moieties are comprised of bis-succinimdylmethylether (BSME), 4-(2,2-dimethylacetyl)benzoic acid (DMAB), tris (succinimidylethyl)amine (TSEA) and N-[2-(N',N'-bis(2-succinimidoethyl)aminoethyl)]-$N^6$,$N^9$-bis(2-methyl-2-mercaptopropyl)-6,9-diazanonanamide (BAT-BS).

The invention also comprises scintigraphic imaging agents that are complexes of the reagents of the invention with Tc-99m, $^{111}$In or $^{68}$Ga, most preferably Tc-99m and methods for radiolabeling the reagents. Tc-99m radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

The invention also provides kits for preparing scintigraphic imaging agents that are the reagents of the invention radiolabeled with Tc-99m. Kits for labeling the reagents provided by the invention with Tc-99m are comprised of a sealed vial containing a predetermined quantity of a reagent of the invention and a sufficient amount of reducing agent to label the reagent with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled reagents for imaging thrombi within a mammalian body by obtaining in vivo gamma scintigraphic images. These methods comprise administering an effective diagnostic amount of Tc-99m labeled reagents of the invention and detecting the gamma radiation emitted by the Tc-99m label localized at the thrombus site within the mammalian body.

Specific preferred embodiments of the present invention will become evident from the following more detailed description of certain preferred embodiments and the claims.

DETAILED DESCRIPTION OF THE INVENTION

The present invention provides reagents, including peptide reagents, for preparing radiolabeled thrombus imaging agents for imaging a thrombus within a mammalian body. The reagents provided by the invention comprise a radiolabel binding moiety covalently linked to a specific binding compound that binds a platelet receptor that is the platelet GPIIb/IIIa receptor and is capable of inhibiting human platelet aggregation in platelet-rich plasma by 50% when present at a concentration of no more than 0.3 μM. For purposes of the invention, the term thrombus imaging reagent will refer to embodiments of the invention comprising a specific binding compound covalently linked to a radiolabel binding moiety and radiolabeled, preferably with Tc-99m, $^{111}$In or $^{68}$Ga, most preferably with Tc-99m.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Another advantage of the present invention is that none of the preferred radionuclides are toxic, in contrast to other radionuclides known in the art (for example, $^{125}$I).

In the Tc-99m binding moieties and compounds covalently linked to such moieties that contain a thiol covalently linked to a thiol protecting groups [(pgp)$^s$] provided by the invention, the thiol-protecting groups may be the same or different and may be but are not limited to:

—CH$_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—CH$_2$-(4-methoxyphenyl);

—CH-(4-pyridyl)(phenyl)$_2$;

—C(CH$_3$)$_3$

—9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$-phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide-containing embodiment of the invention is comprised of a sequence of amino acids. The term amino acid as used in this invention is intended to include all L- and D- amino acids, naturally occurring and otherwise. Specific-binding peptides provided by the invention include but are not limited to peptides having the following sequences (the amino acids in the following peptides are L-amino acids except where otherwise indicated):

(SEQ ID NO.: 1)

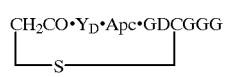

(SEQ ID NO.: 2)

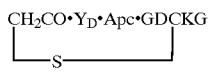

(SEQ ID NO.: 3)

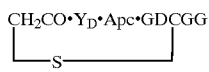

Specific-binding peptides of the present invention can be chemically synthesized in vitro. Peptides of the present invention can generally advantageously be prepared on an peptide synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid [(Pic-); e.g., Pic-Gly-Cysprotecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide capable of specifically binding to a thrombus in vivo, resulting in a radiolabeled peptide having Tc-99m held as neutral complex.

This invention also provides specific-binding small synthetic peptides which incorporate bisamine bisthiol (BAT) chelators which may be labeled with Tc-99m. This invention provides for the incorporation of these chelators into virtually any peptide capable of specifically binding to a thrombus in vivo, resulting in a radiolabeled peptide having Tc-99m held as neutral complex. An example of a small synthetic peptide containing a BAT chelator as radiolabel-binding moiety is provided in the Examples hereinbelow.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the akali metal salts such as the sodium salt, or ammonium salts or lower alkyl ammonium salts.

In a preferred embodiment of the invention, a kit for preparing technetium-labeled peptides is provided. An appropriate amount of the reagent is introduced into a vial containing a reducing agent, such as stannous chloride, in an amount sufficient to label the reagent with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus imaging reagents according to the present invention may be prepared by the addition of an appropriate amount of Tc-99m or Tc-99m complex into the vials and reaction under conditions described in Example 4 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The thrombus imaging reagents provided by the present invention can be used for visualizing thrombi in a mammalian body when Tc-99m labeled. In accordance with this invention, the Tc-99m labeled reagents are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of BAT-BM (N-[2-(N',N'-bis(2-maleimidoethyl)aminoethyl)]-$N^6$,$N^9$-bis(2-methyl-2-triphenylmethylthioprolyl)-6,9-diazanonanamide)

BAT-BM was prepared as follows. BAT acid ($N^9$-(t-butoxycarbonyl)-$N^6$,$N^9$-bis(2-methyl-2-triphenylmethylthiopropyl)-6,9-diazanonanoic acid) (10.03 g, 10.89 mmol) and 75 mL of dry methylene chloride ($CH_2Cl_2$) were added to a 250 mL round-bottomed flask equipped with magnetic stir bar and argon balloon. To this solution was added diisopropyl-carbodiimide (3.40 mL, 21.7 mmol, 199 mole %), followed by N-hydroxy-succinimide (3.12 g, 27.1 mmol, 249 mole %). This solution was observed to become cloudy within 1 h, and was further incubated with stirring for a total of 4 h at room temperature. A solution of tris(2-aminoethyl)amine (30 mL, 200 mmol, 1840 mole %) in 30 mL methylene chloride was then added and stirring continued overnight. The reaction mixture was then concentrated under reduced pressure, and the residue partitioned between ethylacetate (150 mL) and 0.5M potassium carbonate ($K_2CO_3$; 150 mL). The organic layer was separated, washed with brine and concentrated to give the crude product N-[2-(N',N'-bis(2-aminoethyl)aminoethyl)]-$N^9$-(t-butoxycarbonyl)-$N^6$,$N^9$-bis(2-methyl-2-triphenylmethylthiopropyl)-6,9-diazanonanamide as a foam/oil.

This crude product was added to a 1000 mL round-bottomed flask, equipped with magnetic stir bar, containing 300 mL THF, and then 30 mL saturated sodium bicarbonate ($NaHCO_3$), 100 mL water and N-methoxycarbonylmaleimide (6.13 g, 39.5 mmol, 363 mole %) were added. This heterogeneous mixture was stirred overnight at room temperature. THF was removed from the mixture by rotary evaporation, and the aqueous residue was twice extracted with ethylacetate (2×75mL). The combined organic layers of these extractions were washed with brine, dried over sodium sulfate, filtered through a medium frit and concentrated to about 12 g of crude product. Purification by liquid chromatography (250 g silicon dioxide/eluted with a gradient of chloroform→2% methanol in chloroform) afforded 5.3 g of pure product (N-[2-(N',N'-bis(2-maleimidoethyl)aminoethyl)]-$N^9$-(t-butoxycarbonyl)-$N^6$,$N^9$-bis(2-methyl-2-triphenylmethylthiopropyl)-6,9-diazanonanamide) (equivalent to 40% yield), along with approximately 5 g of crude product that can be re-purified to yield pure product. Chemical analysis of the purified product confirmed its identity as BAT-BM as follows:

$^1$H NMR (200 mHz, $CDCl_3$): δ0.91 (12H,s), 1.38 (9H,s), 1.2–1.6 (4H,m), 206 (2H, s), 218 (2H,t,J=7), 2.31 (4H,m), 2.55 (2H,t,J=5), 2.61 (4H,t,J=6), 2.99 (2H, s), 3.0–3.3 (4H, m), 3.46 (4H,t,J=6), 6.49 (—NH,t,J=4), 6.64 (4H,s), 7.1–7.3 (18H,m), 7.6 (12H,t,J=17).

EXAMPLE 2

Synthesis of TMEA [tris(2-maleinmidoethyl)amine]

tris(2-aminoethyl)amine (1.49 mL, 10 mmol) dissolved in 50 mL saturated aqueous sodium bicarbonate and cooled in an ice bath, was treated with N-carbomethoxymaleimide (4.808 g, 31 mmol). The mixture was stirred for 30 min on ice and then for another 30 min at room temperature. The mixture was then partitioned between dichloromethane and water, dried over magnesium sulfate, filtered and evaporated to give 3.442 g of product. Reverse phase thin-layer chromatography (RP-TLC) yielded essentially 1 spot ($R_f$=0.63 in 1:1 acetonitrile: 0.5 M sodium chloride). 3.94 mmol (1.817 g) of this product was dissolved in 20 mL tetrahydrofuran and 20 mL saturated sodium bicarbonate and mixed for 2 h. The reaction mixture was then partitioned between ethyl acetate and water. The organic phase was washed with saturated sodium chloride, dried over magnesium sulfate, and filtered. The ethyl acetate solution was diluted with hexanes and cooled. Solid TMEA was collected by filtration and dried to a yield of 832 mg. Chemical analysis of the product confirmed its identity as TMEA as follows:

$^1$H NMR (CDCl$_3$): 2.65 (tr. 2 H), 3.45 (tr.2 H). 6.64 (s. 2 H).

$^{13}$C NMR (CDCl$_3$), 35.5, 51.5, 133.9, 170.4.

EXAMPLE 3

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/diisopropylethylamine in NMP. Where appropriate, HPLC-purified 2-haloacetylated peptides were cyclized by stirring an 0.1–1.0 mg/mL solution in phosphate or bicarbonate buffer (pH 8) containing 0.5–1.0 mM EDTA for 4–48 hours, followed by acidification with acetic acid, lyophilization and HPLC purification. Where appropriate, Cys-Cys disulfide bond cyclizations were performed by treating the precursor cysteine-free thiol peptides at 0.1 mg/mL in pH 7 buffer with aliquots of 0.006 M K$_3$Fe(CN)$_6$ until a stable yellow color persisted. The excess oxidant was reduced with excess cysteine, the mixture was lyophilized and then purified by HPLC.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF, or 5 to 50 mg/mL peptide in 50 mM sodium phosphate (pH 8)/acetonitrile or THF) with 0.33 molar equivalents of TMEA (tris(2-maleimidoethyl)amine; Example 2) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS adducts were prepared by reacting single thiol-containing peptide (at concentrations of 2 to 50 mg/mL peptide in 50 mM sodium phosphate (pH 8)/acetonitrile or THF) with 0.5 molar equivalents of BAT-BM (N-[2-(N',N'-bis(2-maleimidoethyl)aminoethyl)]-N$^9$-(t-butoxycarbonyl)-N$^6$,N$^9$,-bis(2-methyl-2-triphenylmethylthiopropyl)-6,9-diazanonanamide; Example 1) pre-dissolved in acetonitrile or THF, at room temperature for approximately 1–18 h. The solution was then evaporated to dryness and [BAT-BS]-peptide conjugates deprotected by treatment with 10 mL TFA and 0.2 mL triethylsilane for 1 h. The solution was concentrated, the product adducts precipitated with ether, and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or electrospray mass spectroscopy (ESMS).

EXAMPLE 4

A General Method for Radiolabeling with Tc-99m 0.1 mg of a peptide prepared as in Example 2 was dissolved in 0.1 mL of water or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature or at 100° C. for 15–30 min and then filtered through a 0.2 μm filter.

The Tc-99m labeled peptide purity was determined by HPLC using the following conditions: a Waters DeltaPure RP-18, 5μ, 150 mm×3.9 mm analytical column was loaded with each radiolabeled peptide and the peptides eluted at a solvent flow rate equal to 1 mL/min. Gradient elution was performed beginning with 10% solvent A (0.1% CF3COOH/H$_2$O) to 40% solvent B$_{90}$ (0.1% CF$_3$COOH/90% CH$_3$CN/H$_2$O) over the course of 20 min.

Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

EXAMPLE 5

Platelet Aggregation Inhibition Assays

Platelet aggregation studies were performed essentially as described by Zucker (1989, Methods in Enzymol. 169: 117–133). Briefly, platelet aggregation was assayed with or without putative platelet aggregation inhibitory compounds using fresh human platelet-rich plasma, comprising 300,000 platelets per microlitre. Platelet aggregation was induced by the addition of a solution of adenosine diphosphate to a final concentration of 10 to 15 micromolar, and the extent of platelet aggregation monitored using a Bio/Data aggregometer (Bio/Data Corp., Horsham, Pa.). The concentrations of platelet aggregation inhibitory compounds used were varied from 0.1 to 500 μg/mL. The concentration of inhibitor that reduced the extent of platelet aggregation by 50% (defined as the IC$_{50}$) was determined from plots of inhibitor concentration versus extent of platelet aggregation. An inhibition curve for peptide RGDS was determined for each batch of platelets tested as a positive control.

The results of these experiments are shown in Table I. In Table I, the compounds tested are as follows (RGDS is given as a positive control):

P47 = AcSYGRGDVRGDFC$_{Acm}$GC$_{Acm}$ (SEQ ID NO.: 4)

P97 = GRGDVRGDFKC$_{Acm}$GC$_{Acm}$amide (SEQ ID NO.: 5)

P32 = C$_{Acm}$GC$_{Acm}$RRRRRRRRRGDV (SEQ ID NO.: 6)

P143 = CH$_2$CO—Y$_D$RGDCGGC$_{Acm}$GC$_{Acm}$amide (SEQ ID NO.: 7)

P245 = CH$_2$CO—Y$_D$·Apc·GDCGGC$_{Acm}$GC$_{Acm}$GGF$_D$PRPGamide (SEQ ID NO.: 8)

P63 = AcSYGRGDVRGDFKCTCCA (SEQ ID NO.: 9)

P98 = GRDGVRGDFC$_{Acm}$GC$_{Acm}$amide (SEQ ID NO.: 10)

P81 = CH$_2$CO—Y$_D$RGDCC$_{Acm}$GC$_{Acm}$amide (SEQ ID NO.: 11)

P154 = CH$_2$CO—Y$_D$ApcGDCGGGC$_{Acm}$GC$_{Acm}$amide (SEQ ID NO.: 12)

P381 = (CH$_2$CO—Y$_D$ApcGDCKGC$_{Acm}$GC$_{Acm}$GGC-amide)$_2$—BSME

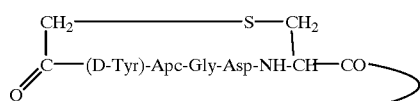
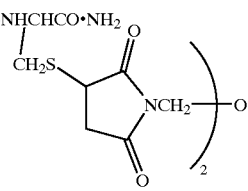

P317 = CH$_2$CO—Y$_D$ApcGDCGGC$_{Acm}$GC$_{Acm}$GGC-amide)$_3$—TSEA

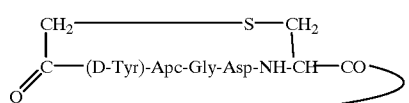
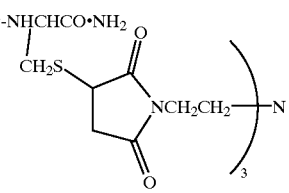

P280 = (CH$_2$CO—Y$_D$ApcGDCGGC$_{Acm}$GC$_{Acm}$GGC-amide)$_2$—BSME

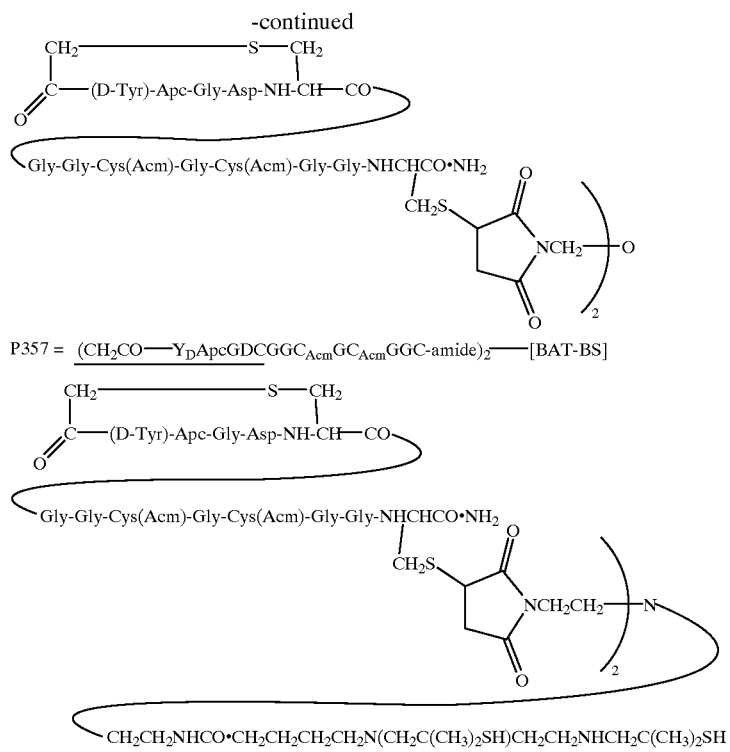

P357 = (CH₂CO—Y_DApcGDCGGC_AcmGC_AcmGGC-amide)₂—[BAT-BS]

(Single-letter abbreviations for amino acids can be found in G. Zubay, Biochemistry (2d. ed.), 1988 (MacMillen Publishing: New York) p.33; Ac=acetyl; Acm=acetamidomethyl; Apc=L-[S-(3-aminopropyl)cysteine; $Y_D$=D-tyrosine; BSME=bis-succinimidylmethylether; TSEA=tris(succinimidylethyl)amine; [BAT-BS]=N-[2-(N',N'-bis(2-succinimidoethyl) aminoethyl]-$N^6$,$N^9$,-bis(2-methyl-2-mercaptopropyl)-6,9-diazanonanamide; peptides are linked to BSME, TSEA or [BAT-BS] linkers via the free thiol moiety of the unprotected cysteine residue (C) in each peptide).

These results demonstrate that the $IC_{50}$ decreases for cyclic peptides as compared with linear ones, and is even less for polyvalent peptide agents as compared with monovalent peptide agents. These results illustrate the efficacy of the multimeric polyvalent antithrombotic agents of the invention at reducing platelet aggregation.

| Peptides | $IC_{50}(\mu M)$** | Clot/Blood* |
|---|---|---|
| P357 | 0.081 | 8.6 ± 3.7[2] |
| P280 | 0.090 | 4.4 ± 1.8[3] |
| P317 | 0.036 | 3.8 ± 2.2[1] |
| P381 | 0.035 | 2.5 |

-continued

| Peptides | $IC_{50}(\mu M)$** | Clot/Blood* |
|---|---|---|
| P154 | 0.3 | 2.0 ± 0.5[1] |
| P245 | 0.5 | 1.5 |
| P143 | 1.3 | 1.4 |
| P97 | 8 | 1.0 |
| P98 | 15 | 1.7 |
| P63 | 19 | 1.7 |
| P47 | 23 | 1.0 |
| P81 | 25 | 1.8 ± 0.6[1] |
| P32 | 26 | 1.2 ± 0.2[2] |

[1] n = 3; [2] n = 4; [3] n = 6
*ratio of (% injected dose/g in a femoral vein thrombus)/(% injected dose/g in blood) at approximately 4h post-injection of each Tc-99m labeled reagent in a canine model of DVT
**concentration of reagent that inhibits by 50% the aggregation of human platelets in platelet-rich plasma induced to aggregate by the addition of adenosine diphosphate (ADP)

It should be understood that the foregoing disclosure emphasizes certain specific embodiments of the invention and that all modifications or alternatives equivalent thereto are within the spirit and scope of the invention as set forth in the appended claims.

What is claimed is:

1. A technetium-99m complex of a reagent comprising a) a glycoprotein IIb/IIIa receptor-binding compound having a molecular weight of less than 10,000 daltons; and b) a radiolabel binding moiety covalently linked to the compound; wherein the reagent binds to a platelet glycoprotein IIb/IIIa receptor with sufficient affinity that said reagent inhibits adenosine diphosphate-induced aggregation of human platelets by 50%, in a standard platelet aggregation assay, when the reagent is present at a concentration of no more than 0.3 $\mu$M.

2. The complex of claim 1, wherein compound is a peptide comprising 4 to 100 amino acids.

3. The complex of claim 2, wherein the radiolabel binding moiety has a formula selected from the group consisting of:

$$\text{Cp(aa)Cp} \qquad \text{I.}$$

wherein Cp is a protected cysteine and (aa) is any primary $\alpha$- or $\beta$-amino acid; a technetium-99m binding moiety comprising a single thiol moiety having a formula:

$$\text{A—CZ(B)—[C(R}^1\text{R}^2\text{)]}_n\text{—X} \qquad \text{II.}$$

wherein

A is H, HOOC, H$_2$NOC, (peptide)—NHOC, (peptide)—OOC or R$^4$;

B is H, SR, —NHR$^3$, —N(R$^3$)-(peptide), or R$^4$;

X is H, SH, —NHR$^3$, —N(R$^3$)-(peptide) or R$^4$;

Z is H or R$^4$;

R$^1$, R$^2$, R$^3$ and R$^4$ are independently H or lower straight or branched chain or cyclic alkyl;

n is 0, 1 or 2;

and where B is —NHR$^3$ or —N(R$^3$)-(peptide), X is SH, and n is 1 or 2;

where X is —NHR$^3$ or —N(R$^3$)-(peptide), B is SH, and n is 1 or 2;

where B is H or R$^4$, A is HOOC, H$_2$NOC, (peptide)—NHOC, (peptide)—OOC, X is SH, and n is 0 or 1;

where A is H or R$^4$, then where B is SH, X is —NHR$^3$ or —N(R$^3$)-(peptide) and where X is SH, B is —NHR$^3$ or —N(R$^3$)-(peptide);

where X is H or R$^4$, A is HOOC, H$_2$NOC, (peptide)—NHOC, (peptide)—OOC and B is SH;

where Z is methyl, X is methyl, A is HOOC, H$_2$NOC, (peptide)—NHOC, (peptide)—OOC, B is SH and n is 0;

and wherein the thiol moiety is in the reduced form;

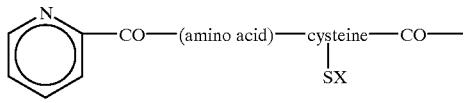 III.

wherein
X=H or a protecting group;
(amino acid)=any amino acid;

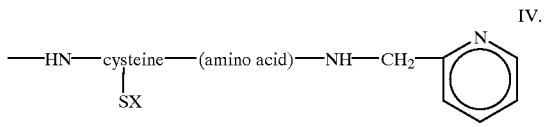 IV.

wherein
X=H or a protecting group;
(amino acid)=any amino acid;

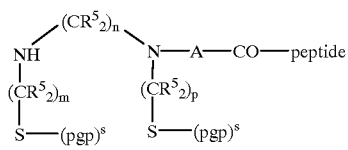 V.

wherein
each $R^5$ is independently H, $CH_3$ or $C_2H_5$;
each $(pgp)^s$ is independently a thiol protecting group or H;
m, n and p are independently 2 or 3;
A=linear lower alkyl, cyclic lower alkyl, aryl, or heterocyclyl, a combination thereof;

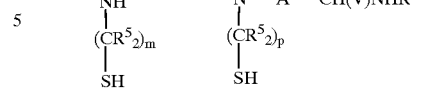 VI.

wherein
each $R^5$ is independently H, lower alkyl having 1 to 6 carbon atoms, phenyl, or phenyl substituted with lower alkyl or lower alkoxy;
m, n and p are independently 1 or 2;
A=linear lower alkyl, cyclic lower alkyl, aryl, or heterocyclyl, a combination thereof;
V=H or —CO-peptide;
$R^6$=H or peptide;
and wherein when V=H, $R^6$=peptide and when $R^6$=H, V=—CO-peptide.

4. The complex of claim 1, wherein the peptide and the radiolabel binding moiety are covalently linked through from one to twenty amino acids.

5. The complex of claim 1, wherein the peptide is selected from the group consisting of:

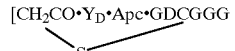 [SEQ ID No.: 1,]

 [SEQ ID No.: 2,]

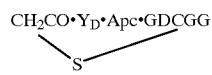 [SEQ ID No.: 3].

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1..3
            (D) OTHER INFORMATION: /label= D-Tyr
                /note= "The tyrosine residue is in the D-stereo-
                chemical configuration"

(ix) FEATURE:
            (A) NAME/KEY: Modified-site
            (B) LOCATION: 1..3
            (D) OTHER INFORMATION: /label= Apc
                /note= "Residue Xaa = L(S-3 aminopropyl)
                cysteine."

(ix) FEATURE:
            (A) NAME/KEY: Modified-site
            (B) LOCATION: 1..5
            (D) OTHER INFORMATION: /label= Cyclic
                /note= "The sidechain sulfur of the Cys
                residue is covalently linked to the amino
                terminus by a -CH2CO- group."

(xi) SEQUENCE DESCRIPTION: SEQ ID NO:1:

Tyr Xaa Gly Asp Cys Gly Gly Gly
1               5

(2) INFORMATION FOR SEQ ID NO:2:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1..3
            (D) OTHER INFORMATION: /label= D-Tyr
                /note= "The tyrosine residue is in the D-stereo-
                chemical configuration"

(ix) FEATURE:
            (A) NAME/KEY: Modified-site
            (B) LOCATION: 1..3
            (D) OTHER INFORMATION: /label= Apc
                /note= "Residue Xaa = L(S-3 aminopropyl)
                cysteine."

(ix) FEATURE:
            (A) NAME/KEY: Modified-site
            (B) LOCATION: 1..5
            (D) OTHER INFORMATION: /label= Cyclic
                /note= "The sidechain sulfur of the Cys
                residue is covalently linked to the amino
                terminus by a -CH2CO- group."

(xi) SEQUENCE DESCRIPTION: SEQ ID NO:2:

Tyr Xaa Gly Asp Cys Lys Gly
1               5

(2) INFORMATION FOR SEQ ID NO:3:

(i) SEQUENCE CHARACTERISTICS:
            (A) LENGTH: 7 amino acids
            (B) TYPE: amino acid
            (D) TOPOLOGY: linear (ii) MOLECULE TYPE: peptide

```
    (ix) FEATURE:
          (A) NAME/KEY: Modified-site
          (B) LOCATION: 1..3
          (D) OTHER INFORMATION: /label= D-Tyr
              /note= "The tyrosine residue is in the D-stereo-
              chemical configuration"

(ix) FEATURE:
          (A) NAME/KEY: Modified-site
          (B) LOCATION: 1..3
          (D) OTHER INFORMATION: /label= Apc
              /note= "Residue Xaa = L(S-3 aminopropyl)
              cysteine."

(ix) FEATURE:
          (A) NAME/KEY: Modified-site
          (B) LOCATION: 1..5
          (D) OTHER INFORMATION: /label= Cyclic
              /note= "The sidechain sulfur of the Cys
              residue is covalently linked to the amino
              terminus by a -CH2CO- group."

(xi) SEQUENCE DESCRIPTION: SEQ ID NO:3:

Tyr Xaa Gly Asp Cys Gly Gly
1               5

(2) INFORMATION FOR SEQ ID NO:4:

(i) SEQUENCE CHARACTERISTICS:
          (A) LENGTH: 15 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= Acetyl amino
              /note= "The amino terminus is modified with an
              acetyl group"

(ix) FEATURE:
          (A) NAME/KEY: Modified-site
          (B) LOCATION: 13..15
          (D) OTHER INFORMATION: /label= Tc-99m-chelator
              /note= "The sidechain sulfur atoms of both Cys
              residues are each protected with an
              acetamidomethyl group"

(xi) SEQUENCE DESCRIPTION: SEQ ID NO:4:

Ser Tyr Gly Arg Gly Asp Val Arg Gly Asp Phe Lys Cys Gly Cys
1               5                   10                  15

(2) INFORMATION FOR SEQ ID NO:5:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 11..13
          (D) OTHER INFORMATION: /label= Tc-99m-chelator
              /note= "The sidechain sulfur atoms of both Cys
              residues are each protected with an
              acetamidomethyl group"

(ix) FEATURE:
          (A) NAME/KEY: Modified-site
          (B) LOCATION: 13
          (D) OTHER INFORMATION: /label= Amide
```

/note= "The carboxyl terminus is modified to an
            amide"

(xi) SEQUENCE DESCRIPTION: SEQ ID NO:5:

Gly Arg Gly Asp Val Arg Gly Asp Phe Lys Cys Gly Cys
1               5                   10

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Tc-99m-chelator
            /note= "The sidechain sulfur atoms of both Cys
            residues are each protected with an
            acetamidomethyl group"

(xi) SEQUENCE DESCRIPTION: SEQ ID NO:6:

Cys Gly Cys Arg Arg Arg Arg Arg Arg Arg Arg Gly Asp Val
1               5                   10                  15

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= D-Tyr
            /note= "The tyrosine residue is in the D-stereo-
            chemical configuration"

(ix) FEATURE:
        (A) NAME/KEY: Modified-site
        (B) LOCATION: 1..5
        (D) OTHER INFORMATION: /label= Cyclic
            /note= "The sidechain sulfur of the Cys
            residue is covalently linked to the amino
            terminus by a -CH2CO- group."

(ix) FEATURE:
        (A) NAME/KEY: Modified-site
        (B) LOCATION: 8..10
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 10
        (D) OTHER INFORMATION: /label= Amide
            /note= "The carboxyl terminus is modified to an
            amide"

(xi) SEQUENCE DESCRIPTION: SEQ ID NO:7:

Tyr Arg Gly Asp Cys Gly Gly Cys Gly Cys
1               5                   10

(2) INFORMATION FOR SEQ ID NO:8:

(i) SEQUENCE CHARACTERISTICS:

(A) LENGTH: 17 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1..3
          (D) OTHER INFORMATION: /label= D-Tyr
              /note= "The tyrosine residue is in the D-stereo-
              chemical configuration"

(ix) FEATURE:
          (A) NAME/KEY: Modified-site
          (B) LOCATION: 1..3
          (D) OTHER INFORMATION: /label= Apc
              /note= "Residue Xaa = L(S-3 aminopropyl)
              cysteine."

(ix) FEATURE:
          (A) NAME/KEY: Modified-site
          (B) LOCATION: 1..5
          (D) OTHER INFORMATION: /label= Cyclic
              /note= "The sidechain sulfur of the Cys
              residue is covalently linked to the amino
              terminus by a -CH2CO- group."

(ix) FEATURE:
          (A) NAME/KEY: Modified-site
          (B) LOCATION: 8..10
          (D) OTHER INFORMATION: /label= Tc-99m-chelator
              /note= "The sidechain sulfur atoms of both Cys
              residues are each protected with an
              acetamidomethyl group"

(ix) FEATURE:
          (A) NAME/KEY: Modified-site
          (B) LOCATION: 11..13
          (D) OTHER INFORMATION: /label= D-Phe
              /note= "The phenylalanine residue is in the D-
              stereochemical configuration"

(ix) FEATURE:
          (A) NAME/KEY: Modified-site
          (B) LOCATION: 17
          (D) OTHER INFORMATION: /label= Amide
              /note= "The carboxyl terminus is modified to an
              amide"

(xi) SEQUENCE DESCRIPTION: SEQ ID NO:8:

Tyr Xaa Gly Asp Cys Gly Gly Cys Gly Cys Gly Gly Phe Pro Arg Pro Gly
1               5                   10                  15

(2) INFORMATION FOR SEQ ID NO:9:

(i) SEQUENCE CHARACTERISTICS:
          (A) LENGTH: 17 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /label= Acetyl amino
              /note= "The amino terminus is modified with an
              acetyl group"

(xi) SEQUENCE DESCRIPTION: SEQ ID NO:9:

Ser Tyr Gly Arg Gly Asp Val Arg Gly Asp Phe Lys Cys Thr Cys Cys Ala
1               5                   10                  15

(2) INFORMATION FOR SEQ ID NO:10:

```
    (i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 10..12
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 12
        (D) OTHER INFORMATION: /label= Amide
            /note= "The carboxyl terminus is modified to an
            amide"

(xi) SEQUENCE DESCRIPTION: SEQ ID NO:10:

Gly Arg Gly Asp Val Arg Gly Asp Phe Cys Gly Cys
1               5                   10

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= D-Tyr
            /note= "The tyrosine residue is in the D-stereo-
            chemical configuration"

(ix) FEATURE:
        (A) NAME/KEY: Modified-site
        (B) LOCATION: 1..5
        (D) OTHER INFORMATION: /label= Cyclic
            /note= "The sidechain sulfur of the Cys
            residue is covalently linked to the amino
            terminus by a -CH2CO- group."

(ix) FEATURE:
        (A) NAME/KEY: Modified-site
        (B) LOCATION: 6..8
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 8
        (D) OTHER INFORMATION: /label= Amide
            /note= "The carboxyl terminus is modified to an
            amide"

(xi) SEQUENCE DESCRIPTION: SEQ ID NO:11:

Tyr Arg Gly Asp Cys Cys Gly Cys
1               5

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: linear
```

```
        (ii) MOLECULE TYPE: peptide (ix) FEATURE:
              (A) NAME/KEY: Modified-site
              (B) LOCATION: 1..3
              (D) OTHER INFORMATION: /label= D-Tyr
                    /note= "The tyrosine residue is in the D-stereo-
                    chemical configuration"

(ix) FEATURE:
              (A) NAME/KEY: Modified-site
              (B) LOCATION: 1..3
              (D) OTHER INFORMATION: /label= Apc
                    /note= "Residue Xaa = L(S-3 aminopropyl)
                    cysteine."

(ix) FEATURE:
              (A) NAME/KEY: Modified-site
              (B) LOCATION: 1..5
              (D) OTHER INFORMATION: /label= Cyclic
                    /note= "The sidechain sulfur of the Cys
                    residue is covalently linked to the amino
                    terminus by a -CH2CO- group."

(ix) FEATURE:
              (A) NAME/KEY: Modified-site
              (B) LOCATION: 9..11
              (D) OTHER INFORMATION: /label= Tc-99m-chelator
                    /note= "The sidechain sulfur atoms of both Cys
                    residues are each protected with an
                    acetamidomethyl group"

(ix) FEATURE:
              (A) NAME/KEY: Modified-site
              (B) LOCATION: 11
              (D) OTHER INFORMATION: /label= Amide
                    /note= "The carboxyl terminus is modified to an
                    amide"

(xi) SEQUENCE DESCRIPTION: SEQ ID NO:12:

Tyr Xaa Gly Asp Cys Gly Gly Gly Cys Gly Cys
1               5                   10
```